(12) United States Patent
Bright

(10) Patent No.: US 10,132,163 B2
(45) Date of Patent: Nov. 20, 2018

(54) MUDLOGGING INJECTION SYSTEM

(71) Applicant: IBALL INSTRUMENTS LLC, Norman, OK (US)

(72) Inventor: Carl Bright, Harrah, OK (US)

(73) Assignee: IBALL INSTRUMENTS, LLC, Norman, OK (US)

(*) Notice: Subject to any disclaimer, the term of this patent is extended or adjusted under 35 U.S.C. 154(b) by 285 days.

(21) Appl. No.: 14/955,447

(22) Filed: Dec. 1, 2015

(65) Prior Publication Data
US 2017/0153211 A1    Jun. 1, 2017

(51) Int. Cl.
| | |
|---|---|
| *G01N 30/16* | (2006.01) |
| *E21B 49/08* | (2006.01) |
| *G01N 30/20* | (2006.01) |
| *G01N 30/32* | (2006.01) |
| *G01N 30/88* | (2006.01) |

(52) U.S. Cl.
CPC ........... *E21B 49/086* (2013.01); *G01N 30/20* (2013.01); *G01N 30/32* (2013.01); *G01N 2030/8854* (2013.01)

(58) Field of Classification Search
CPC ...... E21B 49/086; G01N 30/20; G01N 30/32; G01N 2030/8854
See application file for complete search history.

(56) References Cited

U.S. PATENT DOCUMENTS

| | | | | |
|---|---|---|---|---|
| 4,962,042 A * | 10/1990 | Morabito | ............... | G01N 30/14 422/89 |
| 5,338,514 A * | 8/1994 | Morabito | ............... | G01N 30/12 422/89 |
| 5,611,846 A * | 3/1997 | Overton | ................. | G01N 30/64 73/23.36 |
| 5,670,707 A * | 9/1997 | Fennell | ................. | G01N 30/32 73/19.02 |
| 6,074,461 A * | 6/2000 | Wilson | .................... | G01N 30/28 96/102 |
| 6,974,705 B1 | 12/2005 | Brumboiu et al. | | |
| 7,210,342 B1 | 5/2007 | Sterner et al. | | |
| 7,326,275 B2 | 2/2008 | Begley | | |
| 7,395,691 B2 | 7/2008 | Sterner et al. | | |
| 7,789,159 B1 * | 9/2010 | Bader | .................... | B01D 61/04 166/371 |
| 8,899,348 B2 | 12/2014 | Henderson et al. | | |

(Continued)

OTHER PUBLICATIONS

SRI, MUD-Logging GC system, Nov. 2011.*
(Continued)

*Primary Examiner* — John Breene
*Assistant Examiner* — Mohammad Islam
(74) *Attorney, Agent, or Firm* — Hall Estill Attorneys at Law; Tyler J. Mantooth

(57) ABSTRACT

Assorted apparatus and methods optimize the detection of gas entrapped in drilling fluid. A mudlogging injection system can have a processor that autonomously injects sample gas into a gas chromatograph with near atmospheric pressures to optimize sample gas testing time and accuracy. The processor can autonomously detect errors, such as gas chromatograph detector drift, and conduct chromatograph adjustments to ensure accurate detection of different constituent gases entrapped in the drilling fluid.

20 Claims, 3 Drawing Sheets

(56) References Cited

U.S. PATENT DOCUMENTS

| | | | |
|---|---|---|---|
| 2003/0015019 A1* | 1/2003 | O'Brien | G01N 1/2202 73/23.2 |
| 2003/0079523 A1* | 5/2003 | Lechner-Fish | G01N 30/30 73/23.41 |
| 2007/0169540 A1 | 7/2007 | Sterner et al. | |
| 2007/0272664 A1* | 11/2007 | Schroder | B82Y 30/00 219/121.59 |
| 2008/0217022 A1* | 9/2008 | Deans | E21B 47/12 166/338 |
| 2009/0008560 A1* | 1/2009 | Gunn | G01N 21/3504 250/343 |
| 2012/0118144 A1* | 5/2012 | Cates | G01N 1/2273 95/19 |
| 2013/0270006 A1* | 10/2013 | Selman | E21B 49/005 175/24 |
| 2014/0208840 A1* | 7/2014 | Bright | E21B 49/08 73/152.19 |
| 2016/0010453 A1* | 1/2016 | Breviere | G01N 30/88 175/40 |

OTHER PUBLICATIONS

Bandes et al. Ultrasound simplifies steam trap inspection, 2003.*
Devold, Oil and gas production handbook an introduction to oil and gas production, transport, refining and petrochemical industry, 2013.*

* cited by examiner

MUDLOGGING INJECTION SYSTEM

SUMMARY

A mudlogging injection system, in accordance with various embodiments, has a processor that autonomously injects a measured amount of sample gas into a gas chromatograph at atmospheric pressure, autonomously detects errors in the mudlogging system, and conducts chromatograph adjustments to ensure accurate detection of different constituent gases extracted from drilling fluid. Without limitation, the mudlogging injection system has at least one gas chromatograph system that consists of a detector for detecting separated gasses, a column for separating the gas mix apart, and a sample injection means in which the sample injection is conducted at atmospheric pressures.

DETAILED DESCRIPTION

Figure 1:
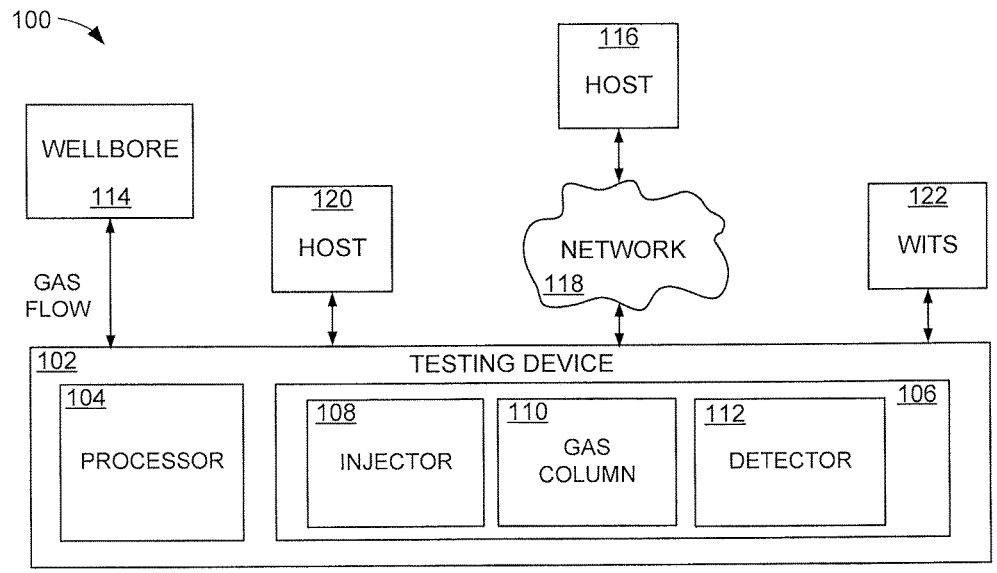
FIG. 1 represents an example mudlogging system arranged in accordance with various embodiments.

With the proliferation of more powerful computational devices, drilling fluid gas sample testing that traditionally was conducted in a laboratory is often performed on an outdoor well site that is exposed to harsh and unpredictable elements. The increase in computing power, reduction of power consumption, and physically smaller sensors allows a mobile computing device to employ a diverse variety of hardware and software components, which can provide greater gas sample testing accuracy and speed than if a gas sample was tested off-site.

In the mudlogging industry, drilling fluids can be tested on-site to detect the amount and types of dissolved gasses within the drilling fluid during the drilling process. A computing device and gas sensing equipment can improve the reliability, speed, and accuracy of the gas sample being tested. However, an overwhelming majority of mudlogging equipment utilized in the mudlogging industry, regardless of infrared detection means, to separate out individual natural gasses during the drilling process are variants of gas chromatography (GC). One such GC means is a packed column style while another is a capillary tube column. On these same systems, many types of detectors can be utilized, such as pellistors, Flame Ionization Detectors (FID), and Thermal Coefficient Detectors (TCD).

One educated in the art of chromatography would find that the variation in speed of gas separations, variation in quality of gas separations, and variation in accuracy of gas separations from a mix of gas presented to the a GC depends on temperature changes, pressure of the mobile phase, chemical makeup of the liquid phase upon the stationary phase as well as the injection method of the sample mix of gas presented to the GC column. Accordingly, various embodiments utilize a mudlogging injection system to efficiently, cheaply, and reliably provide sample gas to a GC and ensure accurate gas detection despite errors in changes in the sample gas and GC over time, such as detector drift.

Currently in the mudlogging industry, different manufacturers go about gas sample injection differently. Some gas injection equipment, although not originally or specifically designed for drilling fluid mudlogging, utilizes an expensive stainless steel rotational gas block valve with up to 10 or more positions that is driven by a stepper motor. These positions allow for the mobile phase to be interrupted and a sample injected without losing pressure upon the column. Other methods can employ individual solenoids to inject sample gas upstream of the compressor where the mobile phase is air. The switching of modes through the rotational gas block can be done under high pressure and with Hydrogen or Helium as a carrier gas.

With this laboratory style and type of equipment in mind, assorted embodiments attach at least two solenoids, a column, switchable pressurized mobile phase, sample gas supply, and dump line to an injection manifold to allow for the insertion of sample gas at the head of the GC column at relative atmospheric pressures. The use of atmospheric pressures during sample gas injection eliminates the need for gas compression or expensive rotational gas blocks that can add considerable complexity, size, and cost to a mudlogging testing system. The tuned position and utilization of at least two solenoids, gas supply, and dump line can allow atmospheric pressures to efficiently move a gas sample into a GC while other methods allow sample testing errors and inaccuracies to be quickly detected and corrected.

FIG. 1 represents an example mudlogging testing system 100 that is arranged in accordance with some embodiments. The testing system 100 has one or more testing devices 102 that can be operated independently and/or concurrently via at least one local processor 104. Each testing device 102 can have one or more chromatograph 106 that contains a sample injector 108, chromatograph column 110, and a detector 112. A gas sample that contains a plurality of different gases separated from drilling fluid is injected by the injector 108 into the column 110. The detector 112 is positioned at the distal end of the column 110 and will detect the separated gasses eluting from the column 110 over time. The detector 112 may be an ultrasonic detector to detect a contaminant.

It is noted that while a gas sample may be procured from any location and environment, assorted embodiments position a testing device 102 no greater than 100 feet from a wellbore 114. The minimal distance from the wellbore 114 to the testing system 100 mitigates damage to the sample line, entrapped gases from escaping or being diluted while traversing to the testing device 102. It is contemplated, but not required, that the testing device 102 is configured to be portable and housed within an explosion-proof case that can be transported by a person without the use of any mechanical equipment, such as a dolly, forklift, or vehicle. Testing device 102 could also be used distally at ranges over 100 feet, such as beyond a hazard zone and placed within a plastic enclosure. The processor 104 can employ the portable case as a heat sink to compensate for temperatures in the portable case.

The ability of the testing device 102 to conduct gas testing operations independently is complemented by the ability to connect to one or more remote host 116 via a wired or wireless network 118. A local host 120, such as a user or connected computed device, may also be utilized to direct operation of the testing device 102. Any remote 116 or local 120 hosts can be a server, node, processor, or other testing device 102 that may be utilized concurrently, redundantly, or successively to improve the accuracy, speed, and breadth of gas sample testing. Any testing device 102 can also be hooked up to a local drilling rig Electronic Drilling Recorder (EDR) that allows the testing device 102 to communicate via duplex communications and a Wellsite Information Transfer System (WITS) connection 122. In this connection configuration the testing device 102 can transmit and receive gas detection information with the drilling rig as well as transmit and receive other drilling rig parameters.

The device processor 104 can conduct continuous, on demand, sporadic, or random measurements of the gas sample as well as the testing environment, such as temperature, humidity, and barometric pressure, with any number of different sensors. Such gas sample and environment monitoring can optimize gas sample testing by adjusting the testing conditions or the apparatus. For example, a detected testing environment can result in gas sample flow, injection amount, and/or pressure being adjusted to the column 110. As another non-limiting example, an encountered testing environment can trigger a testing device processor 104 to alter the generation of injection timing to increase or decrease output to the detector 112. Further device process 104 can further detect the drift or failure of detector 112 and attempt to correct the drift or failure.

Figure 2:
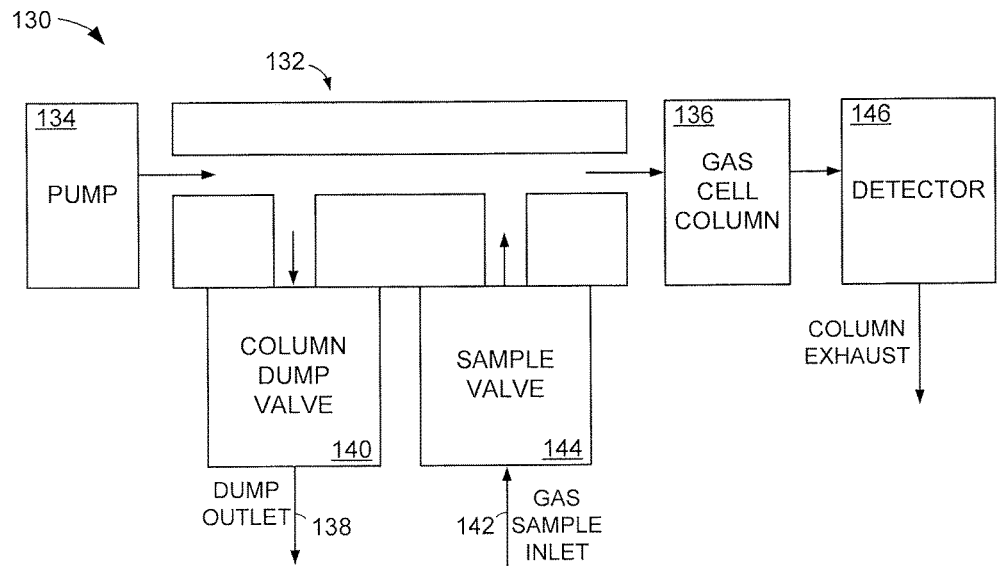
FIG. 2 displays a block representation of a portion of an example gas injection assembly that may be utilized in the mudlogging system of FIG. 1.

FIG. 2 is a block representation of a portion of an atmospheric gas injection assembly 130 that can be employed in the mudlogging testing system 100 in accordance with some embodiments to allow the injection of sample gas at atmospheric pressures. The injection assembly 130 positions an injection manifold 132 between a pump 134 and a GC column 136. The injection manifold 132 has a dump outlet line 138 controlled by a dump valve 140 and a sample gas inlet 142 controlled by a sample valve 144. Although the lines 138 and 142 are labeled respectively as inlet and outlets, such nomenclature does not limit the direction of gas passing into and out of the manifold 132.

Through choreographed operation of the pump 134, dump valve 140, and sample valve 144, atmospheric pressure can force a gas sample into and through the GC column 136 so that one or more detectors 146 can identify the composition and amounts of gases in the gas sample. That is, the detector(s) 146 can detect a plurality of different gases present in the gas sample.

Figure 3A:
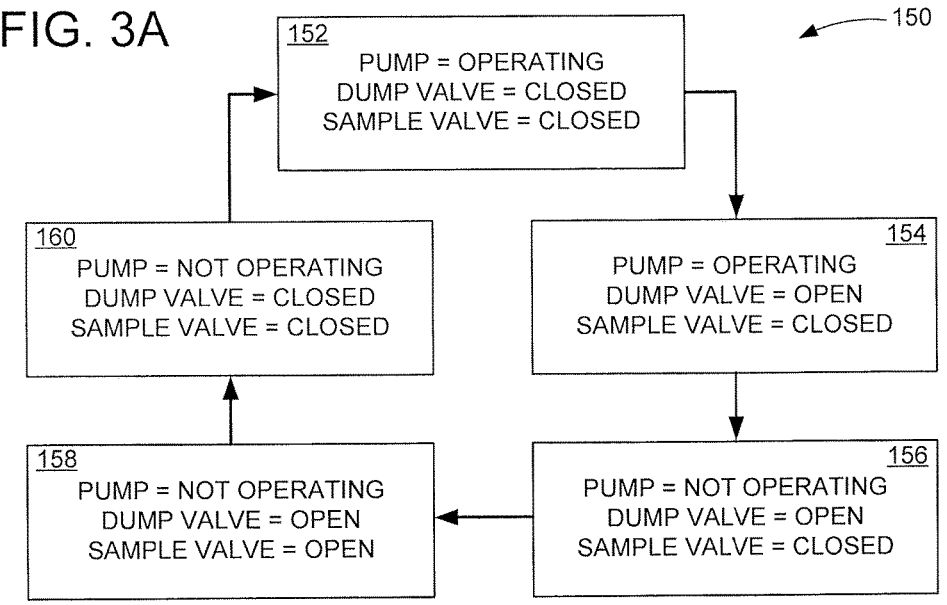
FIGS. 3A and 3B respectively show a flowchart and block representation of an example injection routine carried out in accordance with assorted embodiments.
Figure 3B:
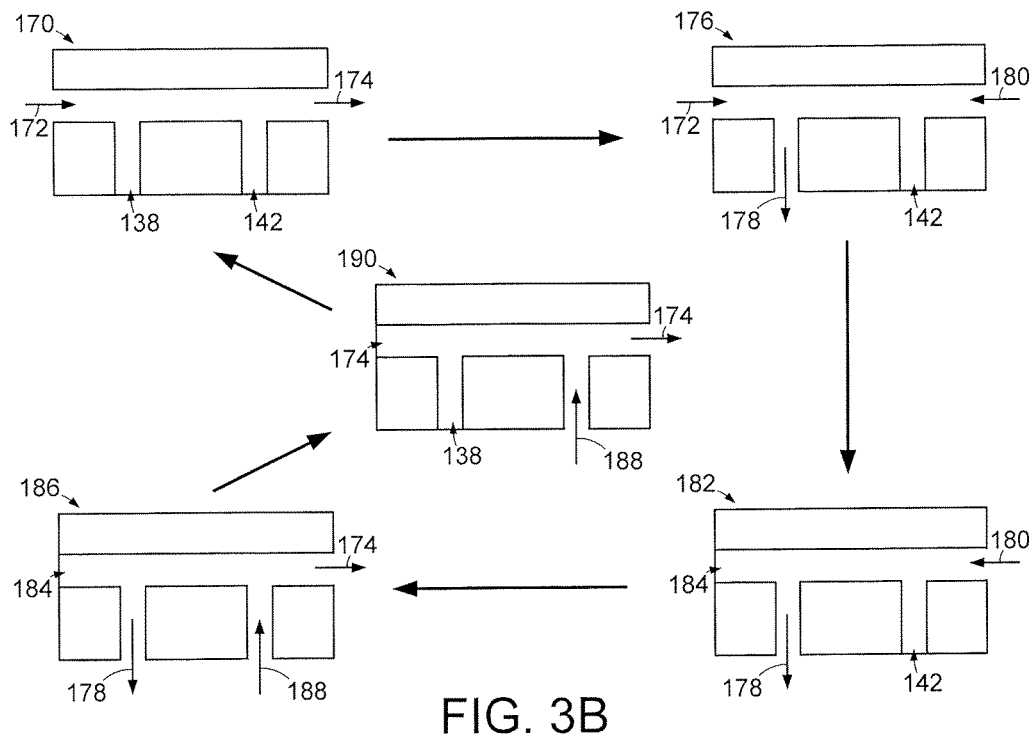

Turning to FIGS. 3A and 3B, flowchart 150 and block representations of an example gas injection routine are illustrated as carried out by the gas injection assembly 130 of FIG. 2. While gas injection can begin with an unlimited variety of equipment configurations, various embodiments initially have a gas sample pump operating while the dump and sample valves are closed, as shown in state 152. Manifold 170 of FIG. 3B corresponds with state 152 and displays how dump outlet 138 and sample inlet 142 are closed while sample gas flow 174 passes from a pressure pump inlet 172 to a GC column head end 174.

In operational state 152, the mobile phase of separated drilling fluid is being presented at operating pressure to the GC column 136 and ultimately to detector 146 along with any separated gasses from any previously injected sample gas. When the dump outlet line 138 is opened, operational state 154 is achieved, as represented by manifold 176 of FIG. 3B. As shown, pressure pump is operating and gas sample flow occurs via the pump inlet 172. The pressure from both the pressure pump and GC column is dumped out the column dump line 178, which corresponds with the reverse flow 180 from the GC column outlet towards the dump line 178. Such flow can remove any trapped water or other contaminates from the manifold, GC column, and column dump line 178.

The removal of pressure from manifold 182 from the pressure pump, as displayed by closed manifold inlet 184 of FIG. 3B, provides operational state 156 where the pressure dump valve 178 is open and sample valve 142 is closed. In this state, any residual pressure from the GC column is dumped out the column dump line 178 and any trapped gasses or contaminates within the injection manifold 182 are also dumped out the column dump line 178. With the manifold 186 and dump line 178 flushed of water and any other contaminates, operational state 158 opens the sample valve allowing sample gas 188 to flow into the manifold 186.

The opening of the sample valve while the pressure pump is not operating results in a light, almost atmospheric, pressure present that pushes the gas sample 188 through the sample valve, into the injection manifold 186, and then out through the open pressure dump valve 178, which loads the manifold 186 with sample gas. Sample gas is unable to escape out the pressure pump due to at least one flow regulator, such as a one way inlet valve, found at the outlet of the pump, and the sample gas is unable to escape out to the GC column due to its normal, almost nonexistent, flow rate at atmospheric pressures.

Closing the dump valve provides operational state 160 where sample gas 188 has filled manifold 190 without the presence of air or other contaminates. It is noted that the sequential flow of sample gas into the manifold 190 via closing the dump valve allows near atmospheric pressure to fill the manifold 190, which is juxtaposed to high pressure (above atmospheric pressure at sea level) sample gas injection techniques.

At the conclusion of operational state 160, the near atmospheric injection of sample gas can cyclically repeat by returning to state 152. At the execution of operational state 152, the sample gas is compressed linearly and introduced or injected into the GC column via outlet 174. As the one knowledgeable in the art of gas chromatography would identify, the injection of sample gas with atmospheric pressure eliminates the need for other common expensive, and complex, injection methodology.

Despite consistent, rapid, and efficient sample gas injection with atmospheric pressure, as illustrated in FIG. 3A, detector errors, such as detector drift, can plague gas chromatography systems over time and exposure to diverse hydrocarbon gasses. Accordingly, various embodiments utilize the atmospheric sample gas injection cycle of FIG. 3A with continuous, on demand, routine, or sporadic sensor monitoring of a chromatography detector to detect current errors and allow a local and/or remote processor to proactively predict and correct for future detector errors. The ability to detect and predict errors, like detector drift, allows a gas chromatography system to adapt and provide consistently accurate sample gas analysis. For example, one or more chromatography sensors, such as a detector, can be adjusted on a periodic basis to keep the output within a specified level and range.

Figure 4:
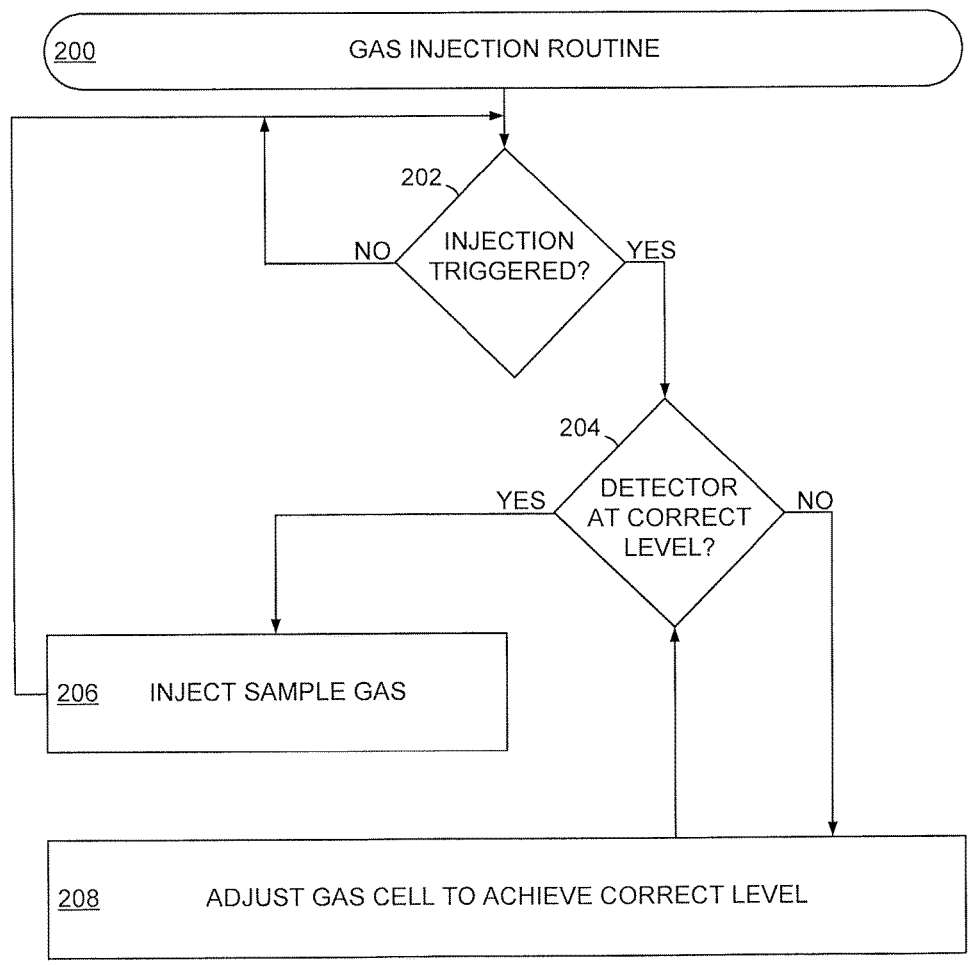
FIG. 4 is an example gas injection routine that may be executed in accordance with some embodiments.

FIG. 4 provides a block diagram of an autonomous gas sampling routine 200 that can be carried out in accordance with assorted embodiments to maintain accurate gas sample analysis. Through routine 200, at least a chromatography detector within a mobile gas chromatography system can be autonomously adjusted to stay within a predetermined level to counter act drifting of the detector over time. It is noted that routine 200 can be conducted with the gas injection assembly 130 of FIG. 2 and the gas injection routine 150 of FIGS. 3A and 3B. In some embodiments, routine 200 is conducted prior to sample gas being injected into a manifold while other embodiments execute routine 200 while sample gas is injected and/or after sample gas is injected into a gas injection assembly.

Initially, routine 200 is timed to execute in conjunction with operational state 152 of FIG. 3A by evaluating in decision 202 whether injection of sample gas has been triggered. If no sample gas is present in the manifold, routine 200 returns to decision 202. In the event sample gas is present in the manifold, decision 204 then determines if one or more gas chromatography detectors is operating at a correct level. For example, decision 204 can perform at least one test on the detector. In another non-limiting example, decision 204 can test the detector by comparing recent and past logged sample gas readings to discover discrepancies and/or trends that can correspond with detector errors.

With the chromatography detector verified operational at pre-defined measurement tolerances and accuracies in decision 204, step 206 proceeds to inject sample gas into a gas cell with atmospheric pressure. However, if the detector is determined to be in a non-predefined state in decision 204, then an autonomous adjustment is made to the detector to bring it into a predetermined state prior to step 206 injecting sample gas into a gas cell. It is contemplated that multiple different adjustments and accuracy tests can be conducted in step 208 to bring a detector into an acceptable operational range. It is further contemplated that decision 204 can determine a detector has malfunctioned and removes the detector from service while activating one or more spare detectors that have been verified as accurate.

Through the utilization of atmospheric pressure injection and autonomous chromatography detector error detection and correction, a mobile gas chromatography system can be consistently employed on a drilling site with minimal maintenance and risk of inaccurate drilling fluid measurements. The ability to detect and correct chromatography measurement errors eliminates the need for specialized personnel on-site and ensures proper corrective actions are taken to provide accurate sample gas readings after a chromatography detector error. In the event a detector error is predicted, the gas chromatography system can make proactive adjustments or alter on-site personnel prior to inaccurate readings being provided, which can save time and operating costs on a functioning hydrocarbon exploration site.

What is claimed is:

1. An apparatus comprising a portable case housing a digital processor, injection manifold, and gas cell, the digital processor configured to pass sample gas through the injection manifold to the gas cell uncompressed and at atmospheric pressure, the sample gas comprising a plurality of different hydrocarbon gasses separated from a drilling fluid.

2. The apparatus of claim 1, wherein the portable case is positioned within 100 feet of a wellbore.

3. The apparatus of claim 1, wherein the portable case is explosion proof.

4. The apparatus of claim 1, wherein the injection manifold comprises a dump line connected to a dump valve and a sample line connected to a sample valve.

5. The apparatus of claim 1, wherein the portable case comprises at least one radio transmitter and receiver.

6. The apparatus of claim 1, wherein the portable case comprises external wiring connections configured to communicate to an external data source.

7. The apparatus of claim 1, wherein the digital processor is adapted to communicate to a secondary dedicated external interface device via a network.

8. A method comprising:
housing a digital processor, chromatography detector, injection manifold, and gas cell in a portable case;
verifying the chromatography detector is accurate with the digital processor;
passing sample gas through the injection manifold uncompressed and at atmospheric pressure in response to the chromatography detector being verified, the sample gas separated from a drilling fluid and comprising a plurality of different hydrocarbons; and
measuring an amount of two different hydrocarbons in the sample gas with the chromatography detector.

9. The method of claim 8, wherein the digital processor reverses a flow of sample gas through the injection manifold in response to detecting an injection.

10. The method of claim 8, wherein the digital processor detects at least one contaminant entering the injection manifold and reverses sample gas flow in the injection manifold to expel the contaminant.

11. The method of claim 8, wherein the portable case comprises a first pump that compresses wet atmosphere into a mobile phase and a second pump that moves the sample gas into the injection manifold at or below atmospheric pressure.

12. The method of claim 8, wherein the measuring is conducted at atmospheric pressure by the chromatography sensor.

13. The method of claim 8, wherein the digital processor fills the injection manifold with the sample gas only with a pressure at or below atmospheric pressure.

14. A method comprising:
housing a digital processor, chromatography detector, injection manifold, and gas cell in a portable case;
detecting an error in the chromatography detector autonomously with the digital processor;
correcting the error autonomously with the digital processor;
verifying the chromatography detector is accurate with the digital processor;
passing sample gas through the injection manifold to a head end of the chromatography detector uncompressed and at no more than atmospheric pressure in response to the chromatography detector being verified, the sample gas separated from a drilling fluid and comprising a plurality of different hydrocarbons; and
measuring an amount of at least two different hydrocarbons in the sample gas with the chromatography detector.

15. The method of claim 14, wherein the apparatus also contains external wiring connections to connect to an external data Well Information Transfer System (WITS).

16. The method of claim 14, wherein the digital processor activates an ultrasonic detector to detect a contaminant in the injection manifold.

17. The method of claim 16, wherein the digital processor reverses flow of the sample gas in the injection manifold in response to the detection of the contaminant.

18. The method of claim 16, wherein the contaminant is water.

19. A method of claim 14, wherein the digital processor autonomously detects a drift in the chromatography detector and corrects the error by altering an output of the chromatography detector.

20. The method in claim 14, wherein the digital processor employs the portable case as a heat sink to compensate for temperatures within the portable case.

* * * * *